United States Patent
Shiley et al.

(10) Patent No.: US 9,618,651 B2
(45) Date of Patent: Apr. 11, 2017

(54) MULTI-SENSOR ANALYSIS OF COMPLEX GEOLOGIC MATERIALS

(71) Applicant: PANalytical Inc, Boulder, CO (US)

(72) Inventors: Daniel A. Shiley, Frederick, CO (US); Brian Curtiss, Boulder, CO (US)

(73) Assignee: PANalytical Inc., Boulder, CO (US)

( * ) Notice: Subject to any disclaimer, the term of this patent is extended or adjusted under 35 U.S.C. 154(b) by 475 days.

(21) Appl. No.: 14/038,622

(22) Filed: Sep. 26, 2013

(65) Prior Publication Data
US 2014/0088876 A1    Mar. 27, 2014

Related U.S. Application Data
(60) Provisional application No. 61/705,760, filed on Sep. 26, 2012.

(51) Int. Cl.
| | |
|---|---|
| *G01V 13/00* | (2006.01) |
| *G01N 33/24* | (2006.01) |
| *G01N 21/3563* | (2014.01) |
| *G01N 21/359* | (2014.01) |
| *G01N 21/65* | (2006.01) |

(Continued)

(52) U.S. Cl.
CPC ........... *G01V 13/00* (2013.01); *G01N 21/359* (2013.01); *G01N 21/3563* (2013.01); *G01N 21/65* (2013.01); *G01N 21/718* (2013.01); *G01N 33/24* (2013.01); *G01N 2021/1734* (2013.01); *G01N 2021/1736* (2013.01); *G01N 2021/3595* (2013.01); *G01N 2201/129* (2013.01); *G01N 2223/616* (2013.01)

(58) Field of Classification Search
CPC ........................................................ G01V 13/00
USPC ............................................................. 702/8
See application file for complete search history.

(56) References Cited

U.S. PATENT DOCUMENTS
| | | |
|---|---|---|
| 4,701,838 A | 10/1987 | Swinkels et al. |
| 5,360,972 A | 11/1994 | Difoggio et al. |
| (Continued) | | |

FOREIGN PATENT DOCUMENTS
| | | |
|---|---|---|
| WO | 2009080049 A1 | 7/2009 |
| WO | 2011035391 A1 | 3/2011 |
| (Continued) | | |

OTHER PUBLICATIONS

Rabbani, Firoozeh, "International Search Report and Written Opinion re Application No. PCT/US2013/062044", Dec. 13, 2013, p. 10, Published in: AU.

(Continued)

*Primary Examiner* — Bryan Bui
(74) *Attorney, Agent, or Firm* — Neugeboren O'Dowd PC

(57) ABSTRACT

Systems and methods for analyzing an unknown geological sample are disclosed. The system may include at least two analytical subsystems, and each of the at least two analytical subsystems provides different information about the geological sample. The data sets from various analytic subsystems are combined for further analysis, and the system includes a chemometric calibration model that relates geological attributes from analytical data previously obtained from at least two analytical techniques. A prediction engine applies the chemometric calibration model to the combined analytical information from the geological sample to predict specific geological attributes in the unknown geological sample.

14 Claims, 6 Drawing Sheets

(51) Int. Cl.
*G01N 21/71* (2006.01)
*G01N 21/17* (2006.01)
*G01N 21/35* (2014.01)

(56) References Cited

U.S. PATENT DOCUMENTS

| | | | | |
|---|---|---|---|---|
| 5,838,008 A | * | 11/1998 | Esler | G01J 3/28 250/339.07 |
| 8,699,022 B2 | * | 4/2014 | McManus | G01N 21/718 356/306 |
| 2004/0084623 A1 | | 5/2004 | Long et al. | |
| 2013/0204531 A1 | * | 8/2013 | McManus | G01N 21/718 702/2 |
| 2016/0018325 A1 | | 1/2016 | Elsoee et al. | |

FOREIGN PATENT DOCUMENTS

| WO | 2011051166 A1 | 5/2011 |
|---|---|---|
| WO | 2014146719 A1 | 9/2014 |

OTHER PUBLICATIONS

Nickits-Etienne, Athina, "International Preliminary Report on Patentability re Application No. PCT/US2013/062044", Apr. 9, 2015, p. 7, Published in: CH.

* cited by examiner

|  |  | Calibration Set | | | Test Set | |
|---|---|---|---|---|---|---|
| Mineral | Data set | PC | RSQ | SECV | RSQ | SEP |
| Muscovite | Spectra + ICP | 4 | 0.95 | 3.34 | 0.96 | 3.02 |
| Muscovite | ICP | 8 | 0.94 | 3.62 | 0.96 | 2.98 |
| Muscovite | Spectra only | 5 | 0.73 | 7.85 | 0.78 | 6.62 |
| Kaolinite | Spectra + ICP | 5 | 0.79 | 2.38 | 0.68 | 2.19 |
| Kaolinite | ICP | 8 | 0.63 | 3.15 | 0.48 | 2.89 |
| Kaolinite | Spectra only | 7 | 0.68 | 2.92 | 0.71 | 2.01 |
| Pyrite | Spectra + ICP | 6 | 0.94 | 1.22 | 0.95 | 0.90 |
| Pyrite | ICP | 7 | 0.95 | 1.15 | 0.96 | 0.83 |
| Pyrite | Spectra only | 6 | 0.40 | 3.89 | 0.53 | 2.89 |
| Quartz | Spectra + ICP | 9 | 0.91 | 3.63 | 0.92 | 3.23 |
| Quartz | ICP | 10 | 0.92 | 3.45 | 0.93 | 3.13 |
| Quartz | Spectra only | 7 | 0.58 | 7.92 | 0.56 | 7.89 |
| Mineral acid consumption | Spectra + ICP | 9 | 0.90 | 7.17 | 0.91 | 7.31 |
| Mineral acid consumption | ICP | 8 | 0.55 | 15.02 | 0.72 | 12.88 |
| Mineral acid consumption | Spectra only | 13 | 0.62 | 13.79 | 0.75 | 12.07 |

FIG. 5

MULTI-SENSOR ANALYSIS OF COMPLEX GEOLOGIC MATERIALS

CLAIM OF PRIORITY UNDER 35 U.S.C. §119

The present Application for Patent claims priority to Provisional Application No. 61/705,760 entitled "SYSTEMS AND METHODS FOR MULTIVARIATE CALIBRATION USING MULTI-SENSOR DATA" filed 26 Sep. 2012, and assigned to the assignee hereof and hereby expressly incorporated by reference herein.

FIELD OF THE INVENTION

The present invention relates to improving the quality and quantity of information that can be obtained from geological samples. In particular, but not by way of limitation, the present invention relates to systems and methods using multi-sensor data streams for obtaining improved qualitative and quantitative information on ore properties that can allow for efficient mine planning and mining related operations.

BACKGROUND OF THE INVENTION

Characterization of minerals is a complex task, which may include measurement of elemental composition, mineralogy, lithology, hardness, and various other chemical or physical parameters. In the context of mining operations for example, mining companies require knowledge of ore properties for both mine planning and operations. Ore mineralogy has a strong influence on cost and efficiency of metal extraction. Ore metallurgical properties also affect the behavior of the ore in processing steps such as crushing, concentration, and extraction.

In a typical ore analysis system, only one analytic data stream is used to predict or measure a parameter. Near-Infrared (NIR) spectroscopy is a molecular technique and has been used for qualitative and quantitative determination of mineral content and for certain metallurgical response parameters. X-ray fluorescence is typically used to produce a measurement of elemental parameters. Similarly, laser-induced breakdown spectroscopy (LIBS) is another method that provides an elemental analysis. Raman spectroscopy, Fourier Transform Infrared (FT-IR) and NIR spectroscopy are molecular techniques and are used for qualitative estimation of some mineral types. Although NIR, FT-IR and Raman spectroscopic techniques have been used for qualitative estimation of minerals, each is useful for a different set of minerals. While any given analytical technique may be able to provide a subset of the required information, in many cases the accuracy and precision of that single analytical technique may be less than optimal. Accordingly, a system and method are needed to address the shortfalls of present technology and improve the quality and quantity of information required for efficient mine planning and mining related operations.

SUMMARY OF THE INVENTION

Aspects of the present invention include a method for analyzing an unknown geological sample. The method includes obtaining an unknown geological sample and analyzing the unknown geological sample with at least two analytic subsystems to obtain two sets of analytic data. The two sets of analytic data are then combined into a single dataset, and attributes of the unknown geological sample are identified by applying a chemometric calibration model to the combined data to predict geological attributes of the sample.

Other aspects include a system for analyzing an unknown geological sample. The system includes at least two analytic subsystems that include a near-infrared analysis subsystem and at least one other analytic subsystem. Each of the at least two analytic subsystems provide different compositional information about the geological sample. The system also includes a previously generated chemometric calibration model based on a database that includes records with combined data from multiple analytic systems that describes geological attributes with this analytic data. A prediction engine utilizes the chemometric model that was based on the records in the chemometric database to predict the composition of the geological attribute.

Yet other aspects include a non-transitory, tangible processor readable storage medium, encoded with processor readable instructions to perform a method for analyzing an unknown geological sample. The method includes obtaining an unknown geological sample and analyzing the unknown geological sample with at least two analytic subsystems to obtain two sets of analytical data. The two sets of analytical data are collected into a combined dataset, and attributes of the unknown sample are identified by applying a chemometric calibration model to the combined data to predict geological attributes of the sample.

Exemplary embodiments of the present invention that are presented are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying drawing wherein:

FIG. 5 illustrates a summary of the different parameters of the calibration model generated using NIR spectra alone, ICP-AES data alone, and using a combination of NIR spectra and ICP-AES data for different minerals and one metallurgical property.

DETAILED DESCRIPTION

Figure 1:
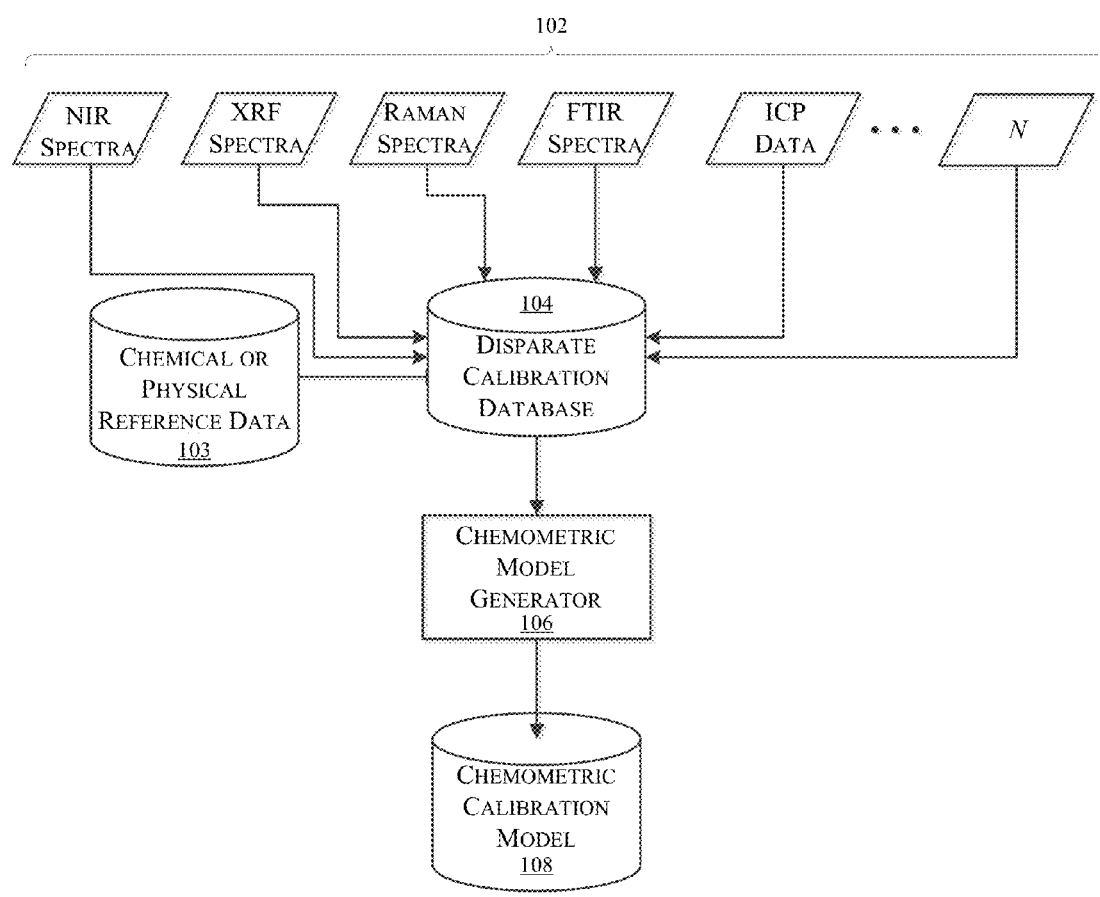
FIG. 1 is a diagram depicting an exemplary system for generating a chemometric calibration model.

Several embodiments disclosed herein provide a method for addressing the need for obtaining improved geological property information by combining data streams and/or results from multiple sensors, such as X-ray diffraction (XRD), X-ray fluorescence (XRF), Raman, Fourier Transform Infrared (FT-IR) spectroscopy, laser-induced breakdown spectroscopy (LIBS), Quantitative Evaluation of Minerals by SCANing electron microscopy (QEMSCAN), whole rock chemistry and near infrared (NIR) into a single multivariate calibration model. For example, NIR, FT-IR and Raman are used to analyze minerals, but each is best suited to a somewhat different list of mineral species. Thus the combination of NIR, FT-IR and Raman sensors is useful together to produce better qualitative and quantitative results.

As discussed above, NIR works well with a wide range of sample preparation approaches. Hence NIR spectra obtained from an NIR spectrometer is combined with data from "whole rock" mineral assays (which are essentially elemental analysis data similar to those produced by XRF instrumentation) or other forms of elemental analysis into a single data matrix for improved chemometric data analysis and calibration development.

In the NIR region many important minerals related to the geologic conditions that are indicative of mineralization (deposit of metal) can be detected. Thus, NIR analytical techniques generally have high utility in connection with measuring alteration minerals. These minerals result from alteration of the host rock and are often pathfinders for mineralization (presence of valuable metals). While the NIR region is sensitive to most alteration minerals, it lacks sensitive to many rock-forming minerals and sulfide minerals, Knowledge of elemental composition can assist in the identification of these minerals, but NIR is a molecular technique. Thus the need often arises to utilize an additional technique to measure the elemental composition of the minerals, such as with Inductively Coupled Plasma-Optical Emission Spectroscopy (ICP-OES) analysis, Inductively Coupled Plasma-Atomic Emission Spectroscopy (ICP-AES), Inductively Coupled Plasma-Mass Spectrometry (ICP-MS), X-ray Fluorescence spectroscopy (XRF) or via various chemical analyses. Additionally, the NIR region is not ideal for measurement of many rock-forming minerals, thus the addition of either Raman or Fourier Transform Infrared (FT-IR) spectroscopy is often separately used. Additional chemical or physical tests may also be used to provide a measure of the metallurgical processing parameters of the materials.

FT-IR analytical techniques typically have utility for measurement of rock-forming minerals, and less utility for alteration minerals. FT-IR is not used for elemental determination. Raman analysis has utility for sulfides, crystalline materials, and some rock-forming minerals, but it is not used for elemental determination. A Raman analytical system uses a laser beam of various wavelengths to excite the atoms of a sample causing them to move into various vibrational states. Some of these vibrational states cause some portion of the incident illumination to have a change in energy. Raman measures the shift in energy state, and materials often have a unique fingerprint for the Raman Shift.

XRF analysis is useful for determination of elemental composition and metal content. XRF is mostly used as a rapid method of elemental analysis, and XRF systems use X-Rays to measure composition. All forms of ICP are used for determination of elemental composition. In mining, ICP is mostly used for determination of metal content.

NIR, FT-IR, Raman and XRF all use electromagnetic radiation to operate. NIR operates in the 350-2500 nm region, FT-IR region includes longer wavelengths whereas XRF instruments operate in the shorter wave region of X-Rays. As those of ordinary skill in the art will appreciate, there is a big overlap between FT-IR, NIR and Raman methods. Typically only one of these methods would be used in mining based primarily on which technique was most suitable for the main mineral of interest.

Referring now to the drawings, where like or similar elements are designated with identical reference numerals throughout the several views, and referring in particular to FIG. 1, it illustrates one embodiment of a system for generating a chemometric calibration model. As shown, in this embodiment N collections of data 102 from N different analytical techniques are each combined with chemical or physical reference data into a disparate calibration database 104. The disparate calibration database 104 is referred to as "disparate" because although the calibration data from the several analytical techniques is accessible, it is still separate at this stage and has not been unified as discussed below.

As depicted, the N collections of data may include NIR spectra, XRF spectra, Raman spectra, FTIR spectra, ICP data from corresponding analytical techniques, and potentially other data from other analytical techniques discussed above and further herein. The chemical or physical reference data 103 in this embodiment is data that represents a known attribute of a geologic sample of matter such as a molecular property or molecular structure. For example, specific mineral content, elemental content, and/or metallurgical properties for a sample may reside in the chemical or physical reference data 103. In this way, a known attribute (e.g., molecular structure) is associated with the corresponding signature of the attribute that is produced by the corresponding analytical technique.

The disparate calibration database 104 may be organized into records and each record may include the known attribute and the corresponding signature produced by the corresponding analytical technique. But when assembled, the disparate calibration database 104 includes a large collection of separate records (separated by analytical techniques); thus the disparate calibration database 104 is useful when analytical techniques are separately used, but is unwieldy, includes redundant data, and is not amenable to use when two or more analytical techniques (e.g., NIR and XRF) are simultaneously used to analyze a sample.

Thus the disparate calibration database 104 represents a collection of typical calibration data that may be utilized with the typical and usual process for materials characterization, which includes separately collecting and analyzing data using a variety of instruments and chemical procedures. In other words, data from each individual analytical technique is stored in the disparate calibration database 104 without regard to the other data (derived compositional or other material property values) from the other analytical techniques.

It should be recognized that the depicted disparate calibration database 104 simply represents the availability of calibration data from the N analytical techniques, and it may be realized by a distributed collection of data stores that may or may not be collocated. For example, it is contemplated that NIR calibration data for a specific geological property may be stored at a first location, and XRF calibration data for the same geological property may be stored at a second location, but the NIR and XRF calibration data are obtainable by wire line and/or wireless networks and provided to the chemometric model generator 106 for processing.

In general, the chemometric model generator 106 functions to combine separate sets of calibration data from the disparate calibration database 104 (corresponding to two or more of the separate analytical techniques) to generate a more comprehensive, yet simpler, characterization of geological attributes of a sample.

Although any given assay may not ideally identify a material, some part of the raw signal or interpreted result may be useful in characterizing other properties of the material. Thus when combined in a multivariate model with other available data, the material can be characterized to a better extent than possible with each individual data source. The combination of all pertinent data (from two or more of the analytical techniques) in the chemometric calibration model 108 enables a better overall characterization of geological sample than with any single source of information. Moreover, the chemometric calibration model 108 is in an easily-actionable form that renders it readily amenable for implementation in mining operations where quick analysis of geologic materials is desired.

In some embodiments, the output (derived compositional or other material property values) from each non-NIR data source is added to the overall database along with NIR spectra. For example, XRF produces a spectrum, which is used by the XRF to determine the elemental composition of a sample. In these embodiments, the elemental values are combined with NIR spectral data into the database to create a multivariate calibration model that is used in the chemometric calibration model 108. In other embodiments, the raw non-NIR data (the XRF spectrum, Raman spectrum, IR spectrum, etc.) (rather than derived compositional or other material property values) are combined with the NIR spectrum to create a multivariate calibration model that is used in the chemometric calibration model 108.

In many instances, the resultant simplified model derived from two sources (e.g., a NIR source and ICP source) result in a characterization that more comprehensively characterizes a geological attribute than the sum of the two separate calibration sets for the sources.

In some implementations, the chemometric model generator 106 is realized by processor-based hardware that executes non-transitory processor executable instructions to combine two or more sets of calibration data into a unified calibration model that is more amenable to application (e.g., to predict a sample's constituent structure and/or components). In some variations, for example, the chemometric model generator 106 utilizes principle component analysis (PCA) to arrive at a model with a number of principle components that is fewer than the number of variables in the source data from the disparate calibration database 104, but it contemplated that other approaches such as partial least squares (PLS) may be utilized.

Figure 2:
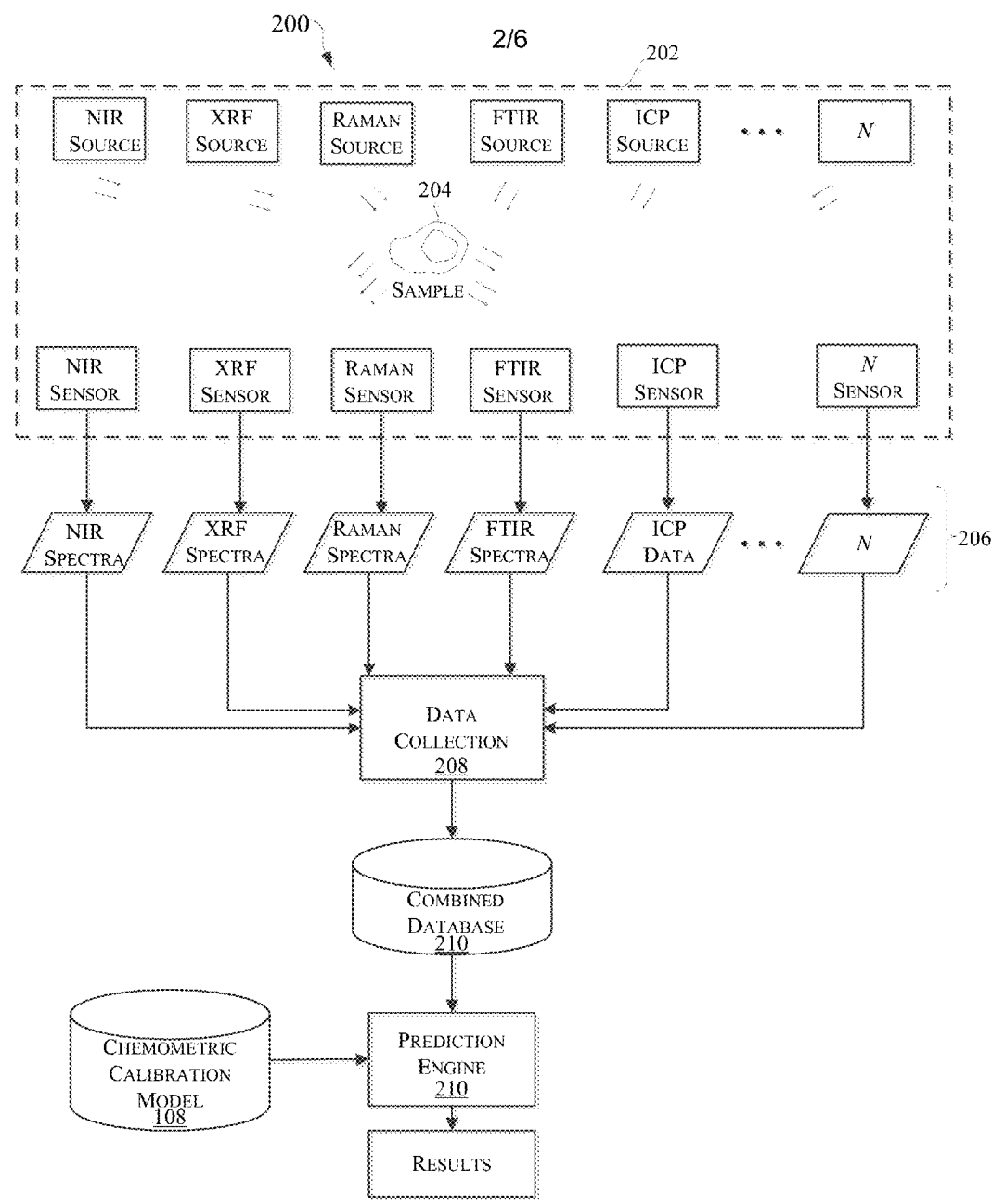
FIG. 2 is a diagram depicting an exemplary system for predicting attributes of an unknown sample using the chemometric calibration model generated in FIG. 1.
Figure 3:
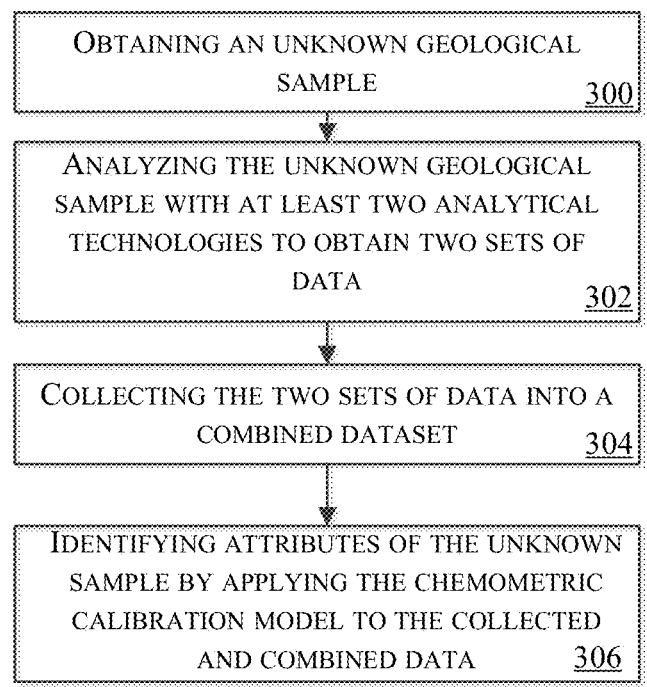
FIG. 3 is a flowchart depicting a method that may be traversed in connection with the embodiment depicted in FIG. 2.

Referring next to FIG. 2, it depicts a system for identifying attributes of a geological sample 204. While referring to FIG. 2, simultaneous reference is made to FIG. 3, which is a flowchart depicting a method that may be traversed in connection with the embodiment depicted in FIG. 2 (in addition to other embodiments described herein). As shown, the system 200 includes an analysis component 202 for analyzing a geological sample (e.g., ore) using two or more of N analytical technologies (also referred to as analytical subsystems) such as NIR, XRF, Raman, FTIR, ICP and potentially other technologies. Although many analytical techniques may be utilized, as discussed further herein, in many embodiments only two analytical technologies are utilized.

In operation, an unknown geological sample is initially obtained for analysis (Block 300). For example, the sample may be an ore sample obtained during the development of a new mine or during ongoing extraction of material from an existing mine. In some mines for example, deposits are spatially variable and ongoing analysis is important for ore sorting or for ore processing optimization. As depicted, the unknown sample is analyzed with at least two of the N analytical technologies (Block 302), and each of the at least two analytical technologies generates a corresponding one of at least two data streams 206 when analyzing the sample.

The data from these streams 206 is then collected in a data collection component 208 before being processed (Block 304). In some implementations, the data from each of the analytical technologies is generated and sent to the data collection component 208 substantially simultaneously. But in other implementations, the analytical technologies do not analyze the sample at the same time, and the data collection component 208 waits until the data from each analytical technology is received before combining and releasing the data to the combined database.

As shown, a prediction engine 212 is coupled to the combined database 210 and the chemometric calibration model 108 (generated as described with reference to FIG. 1), and the prediction engine 210 generally operates to provide an identification of attributes of the sample 204 by applying the chemometric calibration model 108 to the collected and combined data (Block 306). Typically the calibration model consists of a set of vectors that in application are multiplied times the corresponding data vectors to arrive at a predicted result.

It should be recognized that the analytical subsystems are the same types of systems that were used to generate the chemometric calibration model. For example, if the analytical subsystems are NIR and XRF types of systems, then the analytical systems used to generate the chemometric calibration model must also be NIR and XRF systems. One of ordinary skill in the art appreciates that if the analytical subsystems are made by a different manufacturer than the analytical systems used to generate the chemometric calibration model, products are available to convert the data generated by the analytical subsystems so that the chemometric calibration model may be applied to the combined data generated by the analytical subsystems.

In some variations of the embodiment depicted in FIG. 2, the analytical technologies are realized by completely separate machines, which may be manufactured by separate entities. In these embodiments, the data collection component 208 may include hardware or hardware in connection with software in addition to communication links known to those of skill in the art to communicate with the various protocols that are utilized by the different machines. In addition, data is extracted from the various data formats and the data may be converted to different units of measure. One of ordinary skill will also appreciate that the various constructs depicted in FIG. 2 may be connected by wireline or wireless technologies and may be collocated or distributed across different locations.

Figure 4:
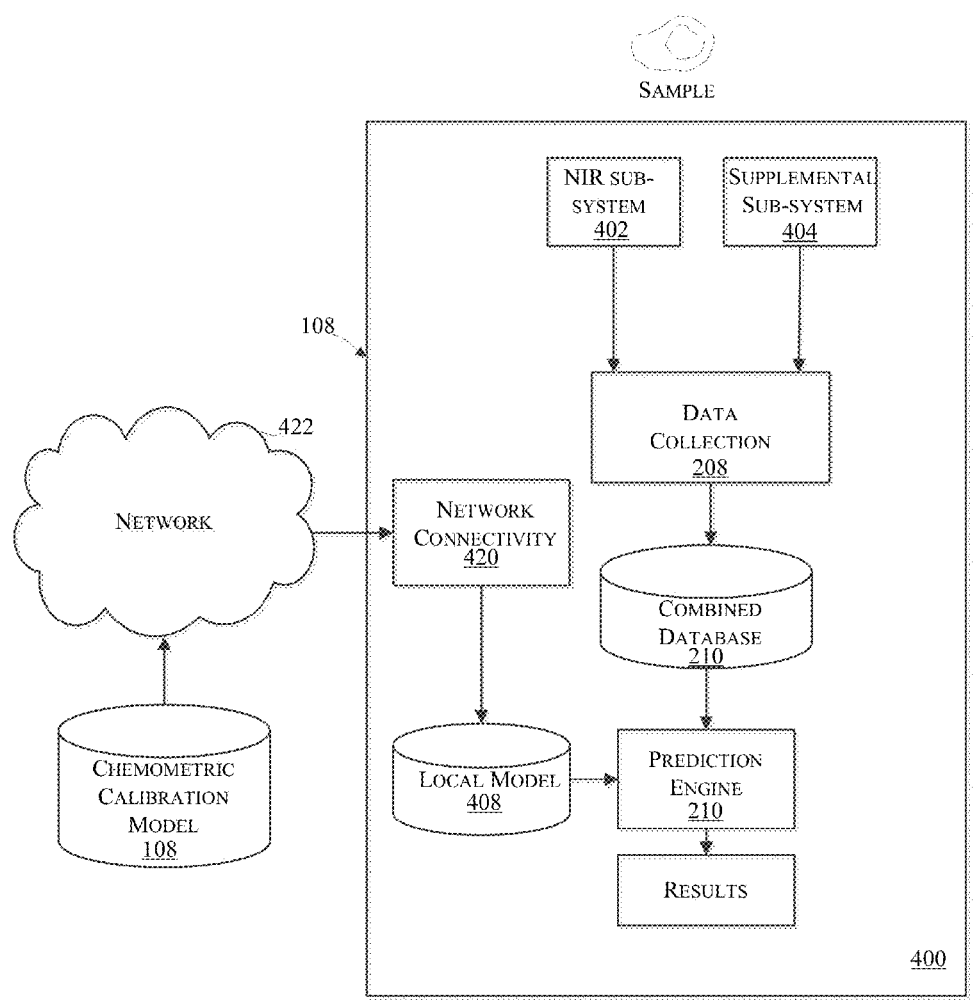
FIG. 4 is a diagram depicting another embodiment in which two or more analytical technologies are integrated in a single unit.

Referring next to FIG. 4, shown is another embodiment in which two or more analytical subsystems are integrated into a single analysis unit 400. Shown are a NIR subsystem and a supplemental subsystem 404 that are coupled to the data collection component 208, which operates as described with reference to FIGS. 2 and 3 to collect and combine data, which is then stored in the combined database 210 for analysis by the prediction component 210 as previously described with reference to FIGS. 2 and 3. As depicted, the analysis unit 400 in this embodiment includes a network connectivity component 420 to enable the analysis unit 400 to receive chemometric calibration data via a network 422 to enable the local chemometric calibration model 408 to be updated.

Although the analysis unit 400 depicted in FIG. 4 only includes two analytical subsystems, other embodiments utilize more than two analytical subsystems. But the depicted use of a NIR subsystem 402 (in connection with at least one other type of analytical subsystem) is an implementation that has wide-ranging utility. More specifically, NIR works well with a wide range of sample preparation approaches, and as a consequence, it is an attractive method to pair with other techniques. In particular, the NIR subsystem 402 is capable of examining irregular surfaces with the same ease as a carefully prepared sample, NIR is non-destructive, and NIR analysis requires little or no sample preparation. NIR can also be used to analyze multiple constituents in a single scan. Combined with another type of analytical subsystem, NIR analysis is an especially powerful tool for a multitude of applications.

Referring to FIG. 5, it is a table depicting a summary of results of an exemplary implementation in which two analytical techniques—NIR spectroscopy and inductively coupled plasma induced atomic emission spectroscopy (ICP-AES)—were utilized to analyze four minerals and one metallurgical property (e.g., mineral acid consumption). As depicted, the four minerals and one metallurgical property (e.g., mineral acid consumption) were modeled using a combination of NIR spectra and ICP-AES data, ICP-AES data alone, and NIR spectra alone, respectively.

Spectral data from an Analytical Spectral Devices, Inc., (ASD) NIR LabSpec 5000 Spectrometer with wavelength range of 350 to 2500 nanometers was combined with data from whole rock inductively coupled plasma induced atomic emission spectroscopy (ICP-AES) analysis. ICP-AES produces elemental data that is similar to data produced by XRF instrumentation. In typical mining operations, the delay between collection of the sample and determination of the traditional ICP-AES data causes a loss in productivity. A drawback of the approach is that it does not allow for real-time process optimization of metal extraction parameters. Thus the inclusion of multiple non-destructive techniques can also enable ore analysis and mine optimization techniques that were previously unattainable.

The column labeled "PC" contains the number of principal components (PC) used in the models that were developed. The PCs are the simplification vectors that are created by various chemometric tools to describe a data matrix. A complex sample set that is not well described by the data may require a large number of PCs, whereas the same sample set described to a better extent will require fewer PCs. Ideally, models should contain the lowest possible number of principal components while producing the lowest possible error.

The number of PCs should be as low as possible and a model with fewer PCs indicates a more simple solution. Fewer PCs are preferred because as PCs are added to describe a data matrix the amount of noise in the PCs tends to increase. Models developed using a higher number of factors are more susceptible to noise in the data and noise in the data can create prediction errors from the models. But if the model is based on a relatively smaller number of factors, generally the models are more robust and less susceptible to prediction errors as the result of noise in the data.

Error of the calibration set is reported as Standard Error of Cross-validation (SECV), which is an estimate of the prediction error that would be encountered on new samples. It is not a measurement of true error because the samples were used in the calibration set, but were iteratively removed and predicted using a calibration that included all remaining calibration set samples. The sample is then added back into the calibration set and the next sample removed and error calculated on the omitted sample. Finally error is averaged across all samples to produce SECV. This is an automated function of all chemometric programs, which mat be utilized in connection with the embodiments disclosed herein. True error as measured by the Standard Error of Prediction is calculated using a set of samples not included in the calibration set. This is the square root of the squared differences divided by the number of samples in the test set. This true error is often used to determine whether the calibration will work as the SECV would indicate it should. As shown in FIG. 5, the number of principle components in many instances was beneficially reduced while the combined use of two analytical techniques (NIR and ICP) provided a more comprehensive analysis of the geological sample.

Of note, quartz and pyrite both have either very low or no (NIR) spectral signature, and hence their calibration models generated via NIR spectra alone were poor. The addition of the supplemental ICP-AES data allowed creation of significantly improved models for these minerals. Note the higher value of the coefficient of determination in calibration ($R^2$—represented by RSQ), the lower value of the standard error in cross validation (SECV), and the lower value of the standard error of prediction (SEP). Additionally, the calibration model obtained for muscovite (one of the key alteration minerals) in the case of NIR spectra alone (RSQ value of 0.73 and a SECV of 7.85) was dramatically improved by using NIR spectra with ICP data (RSQ value of 0.95 and a SECV of 3.34) as seen in FIG. 5.

Mineral and metallurgical models for mining likewise can be significantly improved through the combination of NIR data with XRF data, RAMAN spectra, or (Fourier Transform-Infrared) FT-IR spectra. All of these techniques produce a different data stream that can be combined with NIR spectra (or data) so each is complementary to the NIR spectra. Although, NIR, RAMAN, XRF and FT-IR systems are commonly used as separate systems in mining-related applications, the combination of data from these systems (as performed by the various embodiment disclosed herein) into a single predictive model for mining applications is novel. Additionally, combination of these techniques into a single measurement instrument is also novel.

Figure 6:
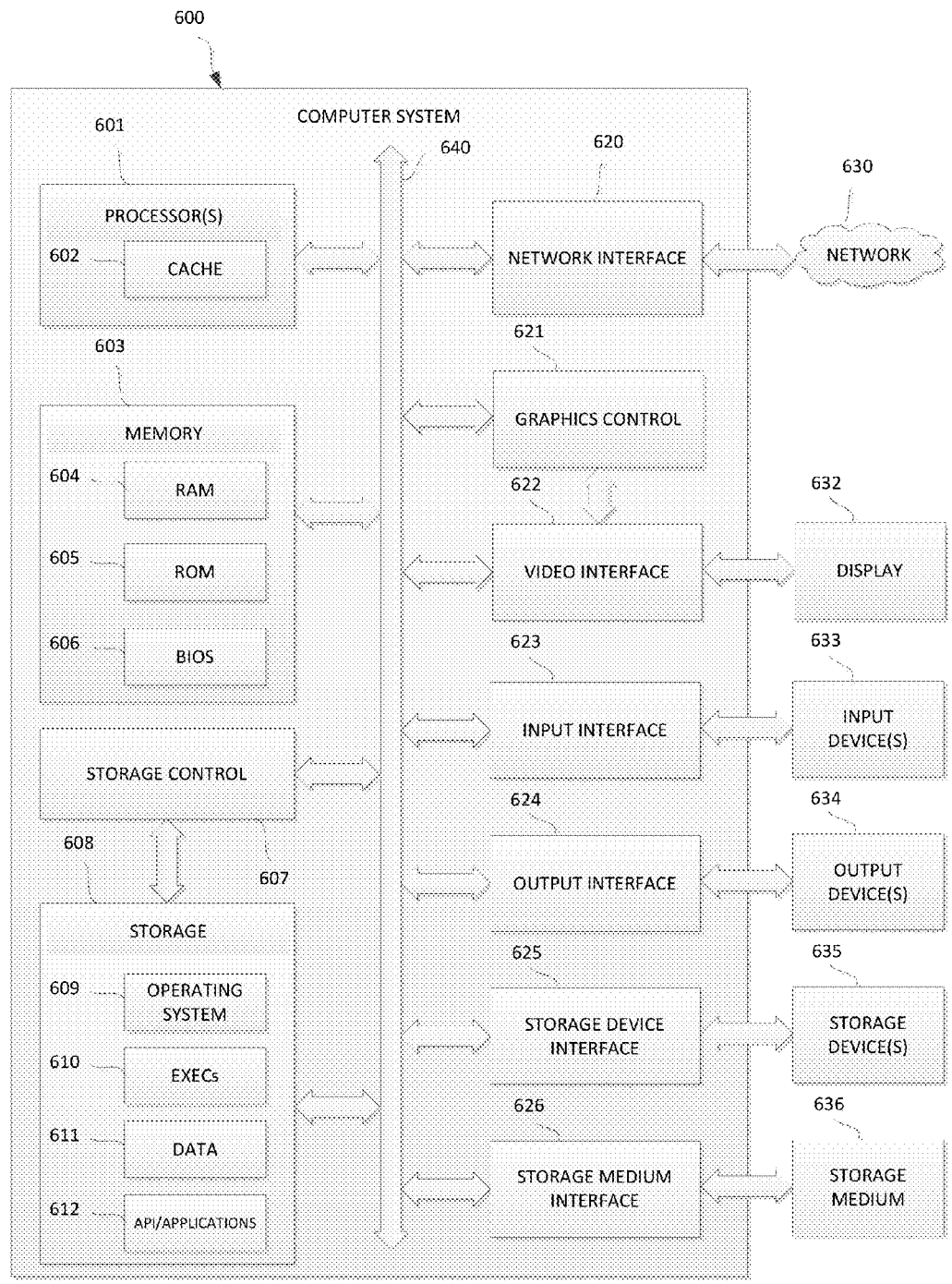
FIG. 6 is block diagram depicting physical components that may be utilized in connection with realizing components disclosed herein.

Aspects of the systems and methods described herein can be implemented in connection with a computer system in addition to the specific physical devices described herein. FIG. 6 shows a diagrammatic representation of one embodiment of a computer system 600 within which a set of non-transitory, processor executable instructions can execute for causing a device to perform or execute any one or more of the aspects and/or methodologies of the present disclosure. For example, the chemometric model generator 106 described with reference to FIG. 1 may be realized in part by a computing device such as that depicted in FIG. 6. In addition, the prediction engine 210 described with reference to FIG. 2 may be realized (at least in part) by components such as those depicted in FIG. 6, and the method described with reference to FIG. 3 may be effectuated (at least in part) by non-transitory, processor-executable instructions that are executed by a system such as the one depicted in FIG. 6. The components in FIG. 6 are examples only and do not limit the scope of use or functionality of any hardware, hardware combined with software, firmware, embedded logic component, or a combination of two or more such components implementing particular embodiments of this disclosure. Some or all of the illustrated components can be part of the computer system 600. For instance, the computer system 600 can be implemented as a general purpose computer (e.g., a laptop computer), mobile device (e.g., tablet or smart phone) or an embedded logic device (e.g., an FPGA), to name just two non-limiting examples.

Computer system 600 includes at least a processor 601 such as a central processing unit (CPU) or an FPGA to name two non-limiting examples. The computer system 600 may also comprise a memory 603 and a storage 608, both communicating with each other, and with other components, via a bus 640. The bus 640 may also link a display 632, one or more input devices 633 (which may, for example, include a keypad, a keyboard, a mouse, a stylus, etc.), one or more output devices 634, one or more storage devices 635, and various non-transitory, tangible computer-readable storage media 636 with each other and with one or more of the processor 601, the memory 603, and the storage 608. All of these elements may interface directly or via one or more interfaces or adaptors to the bus 640. For instance, the various non-transitory, tangible computer-readable storage media 636 can interface with the bus 640 via storage medium interface 626. Computer system 600 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 601 (or central processing unit(s) (CPU(s))) optionally contains a cache memory unit 602 for temporary local storage of instructions, data, or computer addresses. Processor(s) 601 are configured to assist in execution of computer-readable instructions stored on at least one non-transitory, tangible computer-readable storage medium. Computer system 600 may provide functionality as a result of the processor(s) 601 executing software embodied in one or more non-transitory, tangible computer-readable storage media, such as memory 603, storage 608, storage devices 635, and/or storage medium 636 (e.g., read only memory (ROM)). For instance, the method described with reference to FIG. 3 may be embodied in one or more non-transitory, tangible computer-readable storage media. The non-transitory, tangible computer-readable storage media may store software that implements particular embodiments, and processor(s) 601 may execute the software. Memory 603 may read the software from one or more other non-transitory, tangible computer-readable storage media (such as mass storage device(s) 635, 636) or from one or more other sources through a suitable interface, such as network interface 620. The software may cause processor(s) 601 to carry out one or more processes or one or more steps of one or more processes described or illustrated herein. Carrying out such processes or steps may include defining data structures stored in memory 603 and modifying the data structures as directed by the software. In some embodiments, an FPGA can store instructions for carrying out functionality as described in this disclosure. In other embodiments, firmware includes instructions for carrying out functionality as described in this disclosure (e.g., the method described with reference to FIG. 3).

The memory 603 may include various components (e.g., non-transitory, tangible computer-readable storage media) including, but not limited to, a random access memory component (e.g., RAM 604) (e.g., a static RAM "SRAM", a dynamic RAM "DRAM, etc.), a read-only component (e.g., ROM 605), and any combinations thereof. ROM 605 may act to communicate data and instructions unidirectionally to processor(s) 601, and RAM 604 may act to communicate data and instructions bidirectionally with processor(s) 601. ROM 605 and RAM 604 may include any suitable non-transitory, tangible computer-readable storage media described below. In some instances, ROM 605 and RAM 604 include non-transitory, tangible computer-readable storage media for carrying out the methods described herein. In one example, a basic input/output system 606 (BIOS), including basic routines that help to transfer information between elements within computer system 600, such as during start-up, may be stored in the memory 603.

Fixed storage 608 is connected bidirectionally to processor(s) 601, optionally through storage control unit 607. Fixed storage 608 provides additional data storage capacity and may also include any suitable non-transitory, tangible computer-readable media described herein. Storage 608 may be used to store operating system 609, EXECs 610 (executables), data 611, API applications 612 (application programs), and the like. For instance, multiple instances of the storage 608 could be implemented for storage of the disparate calibration database 104, the chemometric calibration model 108, the data collection component 208, and the combined database 210 as described in FIGS. 1, 2, and 4. Often, although not always, storage 608 is a secondary storage medium (such as a hard disk) that is slower than primary storage (e.g., memory 603). Storage 608 can also include an optical disk drive, a solid-state memory device (e.g., flash-based systems), or a combination of any of the above. Information in storage 608 may, in appropriate cases, be incorporated as virtual memory in memory 603.

In one example, storage device(s) 635 may be removably interfaced with computer system 600 (e.g., via an external port connector (not shown)) via a storage device interface 625. Particularly, storage device(s) 635 and an associated machine-readable medium may provide nonvolatile and/or volatile storage of machine-readable instructions, data structures, program modules, and/or other data for the computer system 600. In one example, software may reside, completely or partially, within a machine-readable medium on storage device(s) 635. In another example, software may reside, completely or partially, within processor(s) 601.

Bus 640 connects a wide variety of subsystems. Herein, reference to a bus may encompass one or more digital signal lines serving a common function, where appropriate. Bus 640 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 600 may also include an input device 633. In one example, a user of computer system 600 may enter commands and/or other information into computer system 600 via input device(s) 633. Examples of an input device(s) 633 include, but are not limited to, an alpha-numeric input device (e.g., a keyboard), a pointing device (e.g., a mouse or touchpad), a touchpad, touchscreen, a joystick, a gamepad, an audio input device (e.g., a microphone, a voice response system, etc.), an optical scanner, a video or still image capture device (e.g., a camera), and any combinations thereof. Input device(s) 633 may be interfaced to bus 640 via any of a variety of input interfaces 623 (e.g., input interface 623) including, but not limited to, serial, parallel, game port, USB, FIREWIRE, THUNDERBOLT, or any combination of the above.

In particular embodiments, when computer system 600 is connected to network 630 (such as network 422 in FIG. 4), computer system 600 may communicate with other devices, such as mobile devices and enterprise systems, connected to network 630. Communications to and from computer system 600 may be sent through network interface 620. For example, network interface 620 may receive incoming communications (such as requests or responses from other devices) in the form of one or more packets (such as Internet Protocol (IP) packets) from network 630, and computer system 600 may store the incoming communications in memory 603 for processing. Computer system 600 may similarly store outgoing communications (such as requests or responses to other devices) in the form of one or more packets in memory 603 and communicated to network 630 from network interface 620. Processor(s) 601 may access these communication packets stored in memory 603 for processing.

Examples of the network interface 620 include, but are not limited to, a network interface card, a modem, and any combination thereof. Examples of a network 630 or network segment 630 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 630, may employ a wired and/or a wireless mode of communication. In general, any network topology may be used.

Information and data can be displayed through a display 632. Examples of a display 632 include, but are not limited to, a liquid crystal display (LCD), an organic liquid crystal display (OLED), a cathode ray tube (CRT), a plasma display, and any combinations thereof. The display 632 can interface to the processor(s) 601, memory 603, and fixed storage 608, as well as other devices, such as input device(s) 633, via the bus 640. The display 632 is linked to the bus 640 via a video interface 622, and transport of data between the display 632 and the bus 640 can be controlled via the graphics control 621. The results presented by the prediction engine 210 may be displayed by the display.

In addition to a display 632, computer system 600 may include one or more other peripheral output devices 634 including, but not limited to, an audio speaker, a printer, and any combinations thereof. Such peripheral output devices may be connected to the bus 640 via an output interface 624. Examples of an output interface 624 include, but are not limited to, a serial port, a parallel connection, a USB port, a FIREWIRE port, a THUNDERBOLT port, and any combinations thereof.

In addition or as an alternative, computer system 600 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a non-transitory, tangible computer-readable medium may encompass a circuit (such as an IC) storing software for execution, a circuit embodying logic for execution, or both, where appropriate. The present disclosure encompasses hardware or hardware in connection with software.

Within this specification, the same reference characters are used to refer to terminals, signal lines, wires, etc. and their corresponding signals. In this regard, the terms "signal," "wire," "connection," "terminal," and "pin" may be used interchangeably, from time-to-time, within the this specification. It also should be appreciated that the terms "signal," "wire," or the like can represent one or more signals, e.g., the conveyance of a single bit through a single wire or the conveyance of multiple parallel bits through multiple parallel wires. Further, each wire or signal may represent bi-directional communication between two, or more, components connected by a signal or wire as the case may be.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

In conclusion, improvements in the precision and accuracy of ore property calibration when two or more analytical techniques are combined such as those discussed above. The result is a combined system that provides an accurate and precise analysis of as many of the ore mineralogical and metallurgical properties as is possible. In addition, many variations of the system for obtaining the data are rapid and require only a single prepared ore sample. In addition to the selection of the optimum analytical technologies, the software system that optimizes the calibration using the combined dataset may be tailored to the mineralogy of the ore deposit.

What is claimed is:

1. A system for analyzing an unknown mineralogical sample, the system comprising:
   at least two analytical subsystems including a near-infrared spectral-analysis subsystem to obtain molecular information about the mineralogical sample and at least one other analytical subsystem to obtain elemental information about the mineralogical sample, so each of the at least two analytical subsystems provides different information about the mineralogical sample;
   a data collection component to collect and combine the molecular information and elemental information from the analytical subsystems to create combined analytical information as a set of data vectors in a combined database;

a chemometric calibration model that includes a set of vectors that relate mineralogical attributes to molecular and elemental information previously generated with at least two analytical systems that are the same types of systems as the at least two analytical subsystems;

a prediction engine that multiplies the set of vectors in the chemometric calibration model by corresponding data vectors in the combined database to produce predictions of mineralogical attributes in the unknown mineralogical sample; and a display to display the predictions produced by the prediction engine.

2. The system of claim 1, wherein the at least two analytical subsystems are integrated within a single housing.

3. The system of claim 1, wherein the at least two analytical subsystems are discrete and separately operable units.

4. The system of claim 1, including a network connectivity component to couple the chemometric calibration model with a remote chemometric calibration database.

5. The system of claim 1, wherein the mineralogical attributes are selected from the group consisting of elemental attributes, molecular attributes, mineral content, and metallurgical attributes.

6. The system of claim 1, wherein the at least one other analytical subsystem is a technology selected from the group consisting of X-ray diffraction (XRD), X-ray fluorescence (XRF), Raman, laser-induced breakdown spectroscopy (LIBS), Fourier Transform Infrared (FT-IR), Quantitative Evaluation of Minerals by SCANing electron microscopy (QEMSCAN), Inductively Coupled Plasma-Optical Emission Spectroscopy (ICP-OES) analysis, Inductively Coupled Plasma-Atomic Emission Spectroscopy (ICP-AES), and Inductively Coupled Plasma-Mass Spectrometry (ICP-MS).

7. A method for analyzing an unknown mineralogical sample, the method comprising:

obtaining an unknown mineralogical sample;

analyzing the unknown mineralogical sample with at least two mineralogical-property analytical subsystems to obtain two sets of analytical data, a first set of the analytical data including molecular information about the mineralogical sample and a second set of the analytical data including elemental information about the mineralogical sample;

collecting the two sets of analytical data to form combined data as a set of data vectors in a combined database;

identifying attributes of the unknown mineralogical sample by multiplying a set of vectors in a chemometric calibration model by corresponding data vectors in the combined database to produce predictions of mineralogical attributes of the sample, wherein the calibration model is derived from data collected from analytical systems that are the same types as the analytical subsystems; and displaying the predictions of the mineralogical attributes.

8. The method of claim 7 including:

obtaining the chemometric calibration model from a remote location via a network.

9. The method of claim 7, wherein analyzing the unknown mineralogical sample includes analyzing the unknown mineralogical sample with a near-infrared spectral-analysis subsystem to obtain data indicative of a molecular content of the mineralogical sample.

10. The method of claim 9, wherein analyzing the unknown mineralogical sample includes analyzing the unknown mineralogical sample with an analytic technology that provides an indication of elemental content of the mineralogical sample.

11. A non-transitory, tangible processor readable storage medium, encoded with processor readable instructions to perform a method for processing analyzing an unknown mineralogical sample, the method comprising:

obtaining an unknown mineralogical sample;

analyzing the unknown mineralogical sample with at least two mineralogical-property analytical subsystems to obtain two sets of analytical data, a first set of the analytical data including molecular information about the mineralogical sample and a second set of the analytical data including elemental information about the mineralogical sample;

collecting the two sets of analytical data to form combined data as a set of data vectors in a combined database; and identifying attributes of the unknown mineralogical sample by multiplying a set of vectors in a chemometric calibration model by corresponding data vectors in the combined database to produce predictions of mineralogical attributes of the sample, wherein the calibration model is derived from data collected from analytical systems that are the same types as the analytical subsystems; and displaying the predictions of the mineralogical attributes.

12. The non-transitory, tangible processor readable storage medium of claim 11, wherein the method includes obtaining the chemometric calibration model from a remote location via a network.

13. The non-transitory, tangible processor readable storage medium of claim 11, wherein analyzing the unknown mineralogical sample includes analyzing the unknown mineralogical sample with a near-infrared spectral-analysis subsystem to obtain data indicative of a molecular content of the mineralogical sample.

14. The non-transitory, tangible processor readable storage medium of claim 13, wherein analyzing the unknown mineralogical sample includes analyzing the unknown mineralogical sample with an analytic technology that provides an indication of elemental content of the mineralogical sample.

* * * * *